United States Patent [19]

Shih et al.

[11] Patent Number: 5,000,825
[45] Date of Patent: Mar. 19, 1991

[54] MONOEPOXIDE PURIFICATION

[75] Inventors: T. Thomas Shih, Bryn Mawr; John C. Jubin, Jr., West Chester, both of Pa.

[73] Assignee: Arco Chemical Technology, Inc., Wilmington, Del.

[21] Appl. No.: 533,961

[22] Filed: Jun. 6, 1990

Related U.S. Application Data

[63] Continuation-in-part of Ser. No. 327,876, Mar. 23, 1989, abandoned.

[51] Int. Cl.⁵ .................. B01D 3/40; B01D 3/42; C07D 301/32
[52] U.S. Cl. .................. 203/3; 203/64; 203/70; 549/541; 549/542
[58] Field of Search .................. 203/64, 63, 68, 70, 203/3, DIG. 18; 549/541, 542

[56] References Cited

U.S. PATENT DOCUMENTS

| | | | |
|---|---|---|---|
| 3,265,593 | 8/1966 | Leis et al. | 203/64 |
| 3,337,425 | 8/1967 | Binning et al. | 549/541 |
| 3,578,568 | 5/1971 | Washall | 203/64 |
| 3,838,020 | 9/1974 | Kageyama et al. | 203/64 |
| 4,140,588 | 2/1979 | Schmidt | 549/541 |
| 4,544,454 | 10/1985 | Berg et al. | 203/64 |

OTHER PUBLICATIONS

Weissberger, "Technique of Organic Chemistry", vol. 4, 2nd ed., pp. 468, 469 and 508.
Van Winkle, Matthew et al, "Distillation", McGraw-Hill, pp. 392, 446 and 447.

Primary Examiner—Virginia Manoharan
Attorney, Agent, or Firm—William C. Long

[57] ABSTRACT

A method is provided for the separation by extractive distillation of oxygenated impurities from a monoepoxide while avoiding epoxide loss, wherein lower glycol is used as extractive solvent in amounts so as to provide only up to about 0.3 mol % solvent in the vapor in the extractive distillation zone.

6 Claims, 1 Drawing Sheet

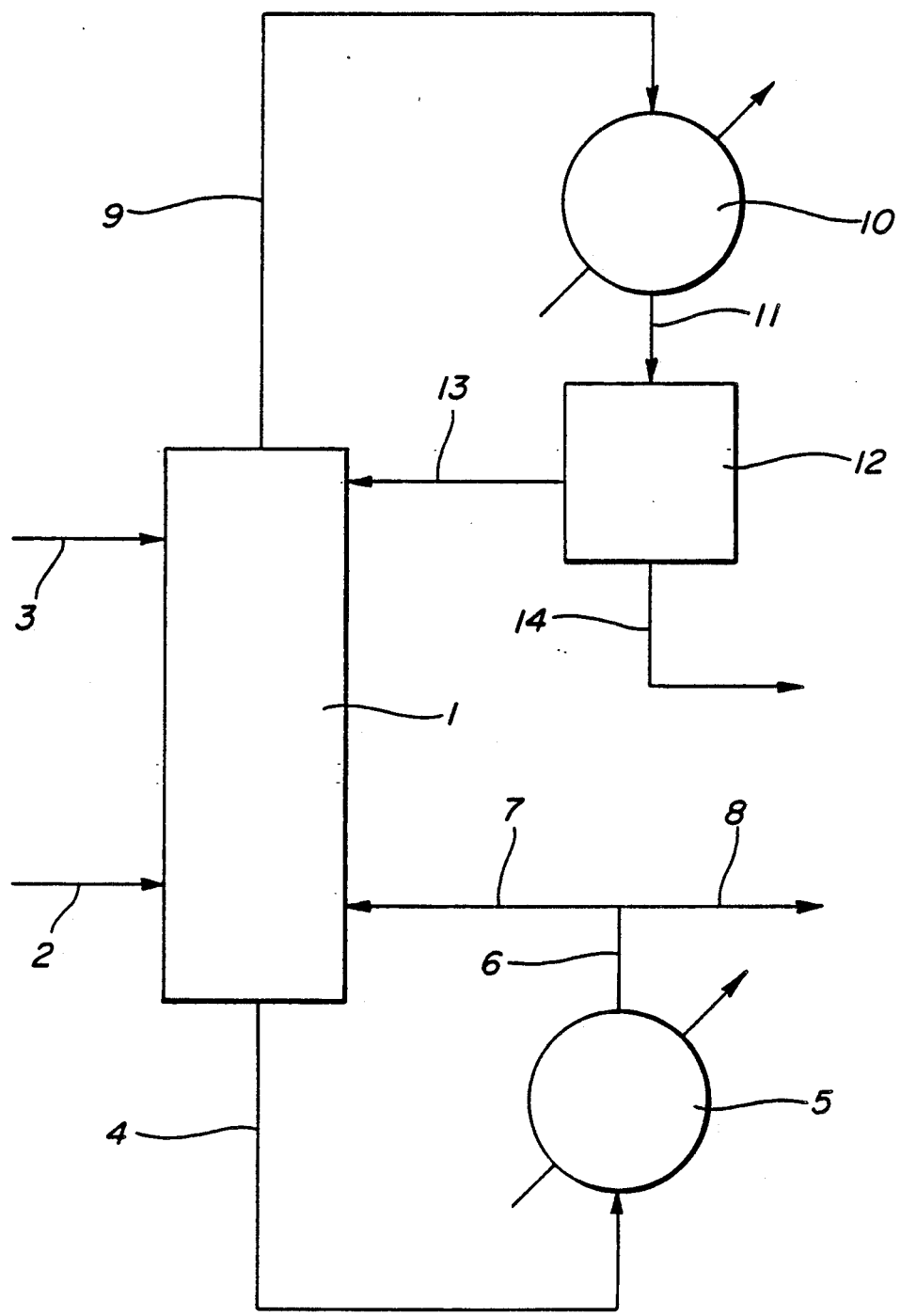

MONOEPOXIDE PURIFICATION

RELATED APPLICATIONS

This application is a continuation-in-part of copending application Ser. No. 07/327,876 filed Mar. 23, 1989, now abandoned.

BACKGROUND OF THE INVENTION

1. Field of the Invention

The present invention relates to the separation of monoepoxides such as propylene oxide from oxygenated impurities by extractive distillation with a lower glycol while avoiding substantial conversion of the monoepoxide.

2. Description of the Prior Art

Monoepoxides such as propylene oxide are highly important chemicals useful in a great number of applications. An important commercial technology for producing the monoepoxides is via the catalytic reaction between the corresponding olefin and an organic hydroperoxide. See, for example, U.S. Pat. No. 3,351,635.

In carrying out this reaction the organic hydroperoxide is reduced to the corresponding alcohol. Also produced, however, are small amounts of other oxygen-containing compounds such as methanol, acetone, acetaldehyde and the like. In general, the alcohol resulting from the reduction of the hydroperoxide can be separated from the epoxide product by ordinary distillation methods, particularly since the organic hydroperoxide employed can be selected to permit this separation. The small amounts of the other oxygenated compounds, however, remain as impurities in the olefin oxide product. For certain of the epoxides, it is extremely important that these impurities be reduced to the low p.p.m. level.

It has previously been proposed to separate these oxygencontaining impurities from the monoepoxide by extractive distillation using lower glycols such as ethylene glycol and propylene glycol. See U.S. Pat. No. 3,578,568 which describes this procedure and which teaches use of solvent in amount to comprise 15 to 50% of the vapor space in the distillation zone. While this previously described separation is quite effective to produce the desired high purity monoepoxide, the methods described result in the loss of small but significant amounts of the valuable monoepoxide by virtue of the reaction between the glycol distillation solvent and the monoepoxide to be purified.

BRIEF DESCRIPTION OF THE INVENTION

In accordance with the present invention, it has been found that monoepoxides containing oxygenated impurities can be purified by extractive distillation using lower glycols without substantial loss of monoepoxide provided that the glycol is used in only minor amounts relative to the impure monoepoxide, i.e., the weight ratio of glycol extractive distillation solvent to distilled monoepoxide is maintained in the range 0.1 to 0.5 and the solvent concentration in the vapor phase in the extractive distillation zone of the distillation column is maintained no higher than about 0.3 mol %. This is to be contrasted, for example, to the working disclosure of U.S. Pat. No. 3,578,568 wherein the effective ratio of glycol extractive distillation solvent to monoepoxide distilled overhead was near 3 and the solvent concentration in the distillation zone was 10 to 50% of the vapor space, i.e. 10 to 50 mol % of the vapor.

BRIEF DESCRIPTION OF THE DRAWINGS

The accompanying drawing illustrates the invention.

DETAILED DESCRIPTION OF THE INVENTION

This invention is applicable to the purification of monoepoxides of olefins having from 3 to 5 carbon atoms. Examples of these compounds are propylene oxide, (1,2-epoxypropane), 1,2-epoxy-butane, 2,3-epoxy-butane; butadiene monoepoxide; 1,2-epoxy-pentane; 2,3-epoxy-pentane; 1,2-epoxy-2-methylbutane; 1,2-epoxy-3-methylbutane; the monoepoxide of the various $C_5$ diolefin isomers and the like.

As has been pointed out, in the preparation of these epoxides there are produced various impurities consisting of such compounds as water, low molecular weight alcohols, low molecular weight ketones, low molecular weight aldehydes and the like. Examples of these low molecular weight compounds are methanol, acetone and acetaldehyde, respectively. These compounds are present in small amounts and since, in general they boil in the same range as the epoxide or form constant boiling mixtures therewith, they are either difficult or impossible to separate by ordinary distillation. These impurities, however, can be removed substantially completely by the method of this invention.

The solvents used in the extractive distillation, as have been described, are lower glycols having 2 to 4 carbon atoms. Preferred glycols are ethylene glycol, 1,2 propane diol and 1,4 butane diol. Other glycols include 1,3 propane diol, 1,2 butane diol, 1,3 butane diol and 2,3 butane diol. Higher diols or higher glycol ethers do not provide sufficient selectivity for the removal of the aforementioned impurities and, therefore, are not included as the extractive distillation solvents suitable for use in this invention.

The method of this invention can be carried out either in a batch system or a continuous system. In the batch system the impure olefin epoxide is introduced into a vessel which can be heated and which is fitted with a fractionation column into which the extractive solvent can be introduced. The extractive solvent is introduced into the fractionating column at a point near the top of the column so that preferably there is some fractionation above the point of introduction in order to prevent carry-over of the extractive solvent with the epoxide. Reflux is also provided. The extractive solvent is suitably introduced at a temperature approximately the same as the boiling point of the mixture in the vessel at the point of introduction.

In the batch process the impure olefin epoxide mixture is heated to boiling and the solvent is introduced into the column in the designated amount. The epoxide substantially free of impurities is withdrawn overhead from the column while the solvent and impurities accumulate in the distillation vessel until finally all of the epoxide or substantially all has been distilled overhead. A reflux ratio of 1:1 to 5:1 generally is sufficient.

In the continuous system the feed consisting of the impure olefin epoxide mixture is introduced into a fractionation tower near the middle or lower section of the tower and the extractive solvent is introduced into the upper section of the tower. The bottom of the tower is generally provided with a reboiler system to provide the necessary heat for fractionation. The bottoms from the tower consisting of the solvent and the impurities such as methanol, acetone, acetaldehyde and the like as has been described, passes through the reboiler where it is heated by indirect exchange or by direct heat and a portion of the bottoms liquid thus heated and partially vaporized is recycled to the lower part of the column. The remaining portion consisting of the impurities and solvent is withdrawn. The overhead vapors consisting of the olefin epoxide substantially free of impurities is withdrawn from the tower and condensed. Usually in accordance with conventional practice a portion of the condensate is returned as recycle or reflux to the top of the tower. Reflux ratios of about 1:1 to 5:1 are likewise appropriate. Such a system is well known in accordance with conventional engineering practices in extractive distillation processes and many modifications thereof are known and can be employed.

Essential to both batch and continuous distillation practices of the invention is the maintenance of very low concentrations of solvent in the extractive distillation sections of the distillation zones. In accordance with the invention, the mol concentration of solvent in the vapor in these sections is maintained not greater that 0.3%; this may be contrasted with the 15 to 50% concentration taught in the prior art.

By maintaining these low solvent concentrations, loss of the monoepoxide through reaction with solvent is essentially avoided while at the same time the solvent, even in such low concentrations is effective in achieving separation of the impurities from the monoepoxide.

One embodiment of the foregoing description of the continuous system is shown in the drawing wherein numeral 1 refers to the fractionation tower or extractive distillation zone which is provided with conventional trays, packing or the like. The impure olefin epoxide mixture is introduced into tower 1 through line 2, and the extractive solvent is introduced into tower 1 through line 3. The bottoms from the tower consisting of the impurities and the solvent is removed through line 4 and passed through reboiler 5 wherein the bottoms are heated. Heated liquid is passed through line 6 and a portion is returned through line 7 to the tower 1 to provide the heat necessary for the distillation. The remaining portion of the bottoms is removed through line 8. The overhead vapors consisting of the olefin epoxide are withdrawn from the tower through line 9 and passed to condenser 10 and from condenser 10 through line 11 to receiver 12. A portion of the condensate can be returned to the top of the tower 1 through line 13, as reflux, and the remainder of the condensate is withdrawn from the receiver 12 through line 14 as purified product.

The following examples are provided to illustrate the invention in greater detail and to demonstrate its utility. It will be understood, however, that the invention is not to be construed as being limited thereto.

EXAMPLE 1

A series of continuous extractive distillation runs were carried out in a fifty (50) tray one inch Oldershaw column with the solvent feed and propylene oxide feed at 15 and 25 trays from the top, respectively. The column was operated at 1 atmospheric pressure. About 250 grams/hr of propylene oxide containing water (3800 to 5510 ppm) and methanol (378 ppm) impurities were fed to the distillation column at 25th tray while monopropylene glycol (1,2 propane diol) or monoethylene glycol was fed to the 15th tray from the top at 50 grams/hr a solvent to feed ratio of 0.2, and between 230 to 240 grams/hr of propylene oxide was taken overhead as products. Table 1 shows the comparative distillation results with and without a glycol solvent.

When no extractive solvent was used (Runs 1a and 1b), water and methanol remained in the overhead propylene oxide product at relative high concentrations. Only 74% and 31% of water and methanol in the feed, respectively, were removed.

When monopropylene glycol (MPG) was used as an extractive agent (Runs 2a, 2b, 3a, 3b), more than 97% each of methanol and water was removed from propylene oxide under the similar conditions. A very high purity of propylene oxide (water < 100 ppm, methanol < 10 ppm) was produced.

Similarly, a very high purity of propylene oxide was produced using monoethylene glycol (MEG) as an extractive agent (Run 4)

TABLE 1

| Run | Solvent/PO Weight Ratio | Reflux Ratio | Solvent Concentration In Vapor Phase In Extractive Distillation Section Of Column, mol % | Ovhd. Product, ppm Methanol | Water |
| --- | --- | --- | --- | --- | --- |
| 1a*   | 0         | 3   | 0   | 262  | 940 |
| 1b*   | 0         | 3   | 0   | 258  | 980 |
| 2a**  | 0.2 (MPG) | 3   | 0.1 | <10  | 86  |
| 2b**  | 0.2 (MPG) | 3   | 0.1 | <10  | 59  |
| 3a**  | 0.2 (MPG) | 1.5 | 0.2 | <10  | 87  |
| 3b**  | 0.2 (MPG) | 1.5 | 0.2 | <10  | 96  |
| 4***  | 0.2 (MEG) | 3   | 0.1 | <10  | 71  |

*3800 ppm water in feed
**5510 ppm water in feed
***5500 ppm water, 380 ppm methanol in feed

EXAMPLE 2

Distillation runs in Example 1 were repeated with a MPG/feed ratio of 0.8 to 1.5 and a reflux ratio of 3. Concentration of solvent in the vapor phase in the extractive distillation section of the column ranged from about 0.35 to 0.57 mol %. The results show that over 98% each of methanol and water removal from propylene oxide was possible and a very high purity of propylene oxide ($H_2O$ < 100 ppm, methanol < 10 ppm) was produced. However, about 2 to 4 wt% of propylene oxide charged to the distillation column was lost due to reaction versus about 0.3% lost where a glycol/feed ratio was only 0.2 and solvent concentration in the vapor phase in the extractive distillation section of the column was maintained in the range 0.1 to 0.2 mol % in Runs 2a–4 described above.

EXAMPLE 3

Distillation runs in Example 2 are repeated using 1,4 butane diol as extractive solvent in a fifty (50) tray two-inch Oldershaw column. The column is operated at 1 atmosphere pressure. The temperatures at the column top and bottom are 35° C. and 86° C. respectively. About 995 grams/hr. of propylene oxide containing water (5000 ppm) and methanol (400 ppm) impurities are fed into the distillation column at the 25th tray while 1,4 butane diol is fed to the 15th tray from the top at a rate of 200 grams/hr., a solvent to feed ratio of 0.2. At this ratio the concentration of solvent in the vapor phase in the extractive distillation section of the column ranges from about 0.0015 to 0.0018 mol%. Reflux ratio is 1.0. About 950 grams/hr. of propylene oxide is taken overhead, representing over 95% recovery of propylene oxide, as product. The results show that over 98% each of methanol and water are removed from the propylene oxide, and a very high purity propylene oxide product ($H_2O < 10$ ppm, methanol $< 10$ ppm) is recovered.

Based on the propylene oxide content of the overhead and bottoms streams, loss of propylene oxide is less than 0.1%.

What is claimed is:

1. In an extractive distillation process for the separation of oxygenated impurities selected from a group consisting of water, low molecular weight alcohols, low molecular ketones, low molecular weight aldehydes and mixtures thereof from a monoepoxide of an olefin having 3 to 5 carbon atoms containing said impurities using a lower glycol extractive distillation solvent, the improvement which comprises:

(a) introducing impure monoepoxide containing said oxygenated impurities into an intermediate section of an extractive distillation zone, (b) introducing lower glycol extractive distillation solvent into the upper section of said extractive distillation zone up to 0.3 mol % solvent in the vapor phase in the extractive distillation zone so that loss of said monoepoxide is substantially avoided, and (c) distilling monoepoxide substantially free of said oxygenated impurities overhead from said extractive distillation zone.

2. The process of claim 1 wherein the monepoxide is propylene oxide.

3. The process of claim 1 wherein the lower glycol is monoethylene glycol.

4. The process of claim 1 wherein the lower glycol is monopropylene glycol.

5. The process of claim 1 wherein the lower glycol is 1,4 butane diol.

6. In an extractive distillation process for the separation of oxygenated impurities selected from a group consisting of water, methanol, acetone, acetaldehyde and mixtures thereof from propylene oxide containing said impurities using a lower glycol extractive distillation solvent, the improvement which comprises:

(a) introducing impure propylene oxide containing said oxygenated impurities into an intermediate section of an extractive distillation zone, (b) introducing lower glycol extractive distillation solvent into the upper section of said extractive distillation zone, maintaining up to 0.3 mol % solvent in the vapor phase in the extractive distillation zone so that loss of said propylene oxide is substantially avoided, and (c) distilling propylene oxide substantially free of said oxygenated impurities overhead from said extractive distillation zone.

* * * * *